United States Patent
Lee

(10) Patent No.: US 8,457,276 B2
(45) Date of Patent: Jun. 4, 2013

(54) NON-DESTRUCTIVE DETECTION METHOD FOR DETECTING STATE OF SOLDER BALL

(75) Inventor: Wei-Chiang Lee, Taipei Hsien (TW)

(73) Assignee: Hon Hai Precision Industry Co., Ltd., New Taipei (TW)

(*) Notice: Subject to any disclaimer, the term of this patent is extended or adjusted under 35 U.S.C. 154(b) by 334 days.

(21) Appl. No.: 12/939,101

(22) Filed: Nov. 3, 2010

(65) Prior Publication Data

US 2011/0182405 A1    Jul. 28, 2011

(30) Foreign Application Priority Data

Jan. 26, 2010  (TW) .............................. 99101999 A

(51) Int. Cl.
*G01B 15/08* (2006.01)
*G01N 23/18* (2006.01)

(52) U.S. Cl.
USPC ............................................ 378/58; 250/304

(58) Field of Classification Search
USPC ...... 378/57, 58, 204, 210; 250/304, 306–308, 250/358.1, 370.01, 370.08, 370.09, 371, 395, 431, 526; 438/14, 18; 257/48
See application file for complete search history.

(56) References Cited

U.S. PATENT DOCUMENTS

| 4,172,224 A | 10/1979 | Lapinski et al. |
| 5,651,493 A * | 7/1997 | Bielick et al. ................. 228/105 |
| 6,342,400 B1 * | 1/2002 | DePetrillo ....................... 438/15 |
| 2005/0018898 A1 * | 1/2005 | White et al. .................. 382/145 |

* cited by examiner

Primary Examiner — Anastasia Midkiff
(74) Attorney, Agent, or Firm — Altis Law Group, Inc.

(57) ABSTRACT

A detection method detects cracks with small thickness and solder voids with small volume in a solder ball. The method immerses a washed solder ball into a high absorption material solution for a first predetermined time period. The immersed solder ball is then dried in a vacuum chamber at a fixed temperature for a second predetermined time period. Materials of the high absorption material solution of the solder ball are removed by a low absorption material solution. An X-ray machine then detects the cracks and the solder voids in the solder ball.

10 Claims, 5 Drawing Sheets

NON-DESTRUCTIVE DETECTION METHOD FOR DETECTING STATE OF SOLDER BALL

BACKGROUND

1. Technical Field

Embodiments of the present disclosure relate to object detection, and more particularly to a non-destructive detection method for detecting a state of a solder ball.

2. Description of Related Art

During manufacture of electronic products, a circuit device and a printed circuit board are often connected therein using solder balls. FIG. 1 is a partial cross section showing an upper board 100 and a lower board 200 connected by a solder ball 10. For example, the upper board 100 can be one side surface of the circuit device and the lower board 200 can be the printed circuit board. An upper contacting portion 150 is positioned between the upper board 100 and the solder ball 10. A lower contacting portion 450 is positioned between the lower board 200 and the solder ball 10. The manufacturing process sometimes makes an incomplete solder ball 10 including a solder void 50 and a crack 60.

Common techniques for detecting the solder void 50 and crack 60 includes two methods. One method is a red ink detection method and the other method is an X-ray tomography method. In the red ink detection method, the solder ball 10 is immersed into a red ink and a mechanical force separates a detected portion of the solder ball 10. Then, a microscope is used to observe a penetration situation of the red ink of the detected portion of the solder ball 10. However the red ink detection method is a destructive method and the immersed solder ball 10 cannot be detected repeatedly.

FIG. 2 is a horizontal scanography image detected by an X-ray machine of FIG. 1. The solder ball 10 is shown as a circular line. The upper contacting portion 150 and the lower contacting portion 450 are shown as two circular dotted lines. In the X-ray tomography method, the solder void 50 and the crack 60 are detected by an X-ray machine. If a thickness of material of the solder ball 10 is increased, an X-ray absorption of the material of the solder ball 10 is increased. As shown in FIG. 2, the solder void 50 is detected as the circular dotted line in the horizontal scanography image detected by an X-ray machine. However, the crack 60 may be too small that the X-ray machine cannot detect them.

DETAILED DESCRIPTION

Figure 1:
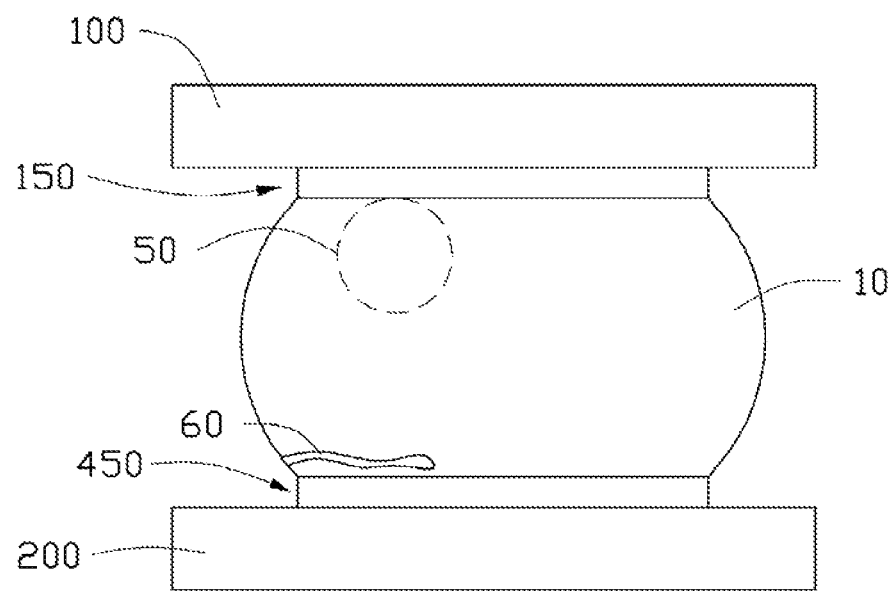
FIG. 1 is one embodiment of a partial cross section showing two boards connected by a solder ball.
Figure 2:
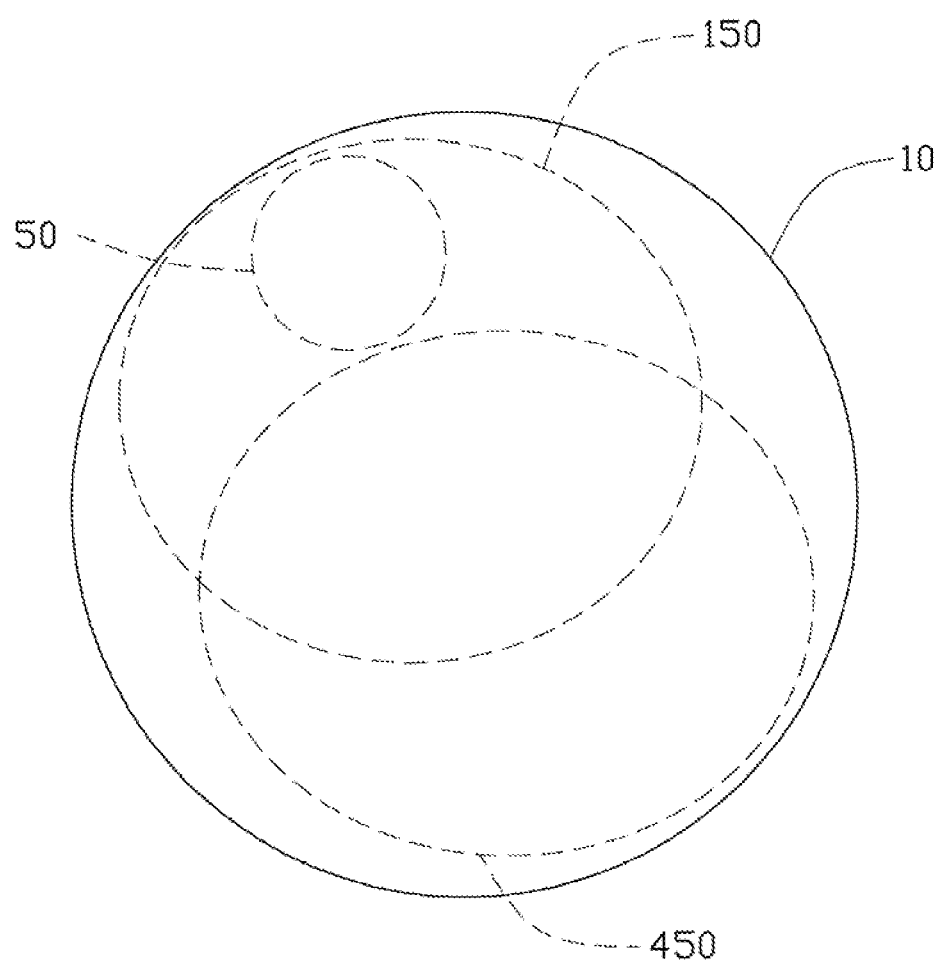
FIG. 2 is one embodiment of a horizontal scanography image detected by an X-ray machine.
Figure 3:
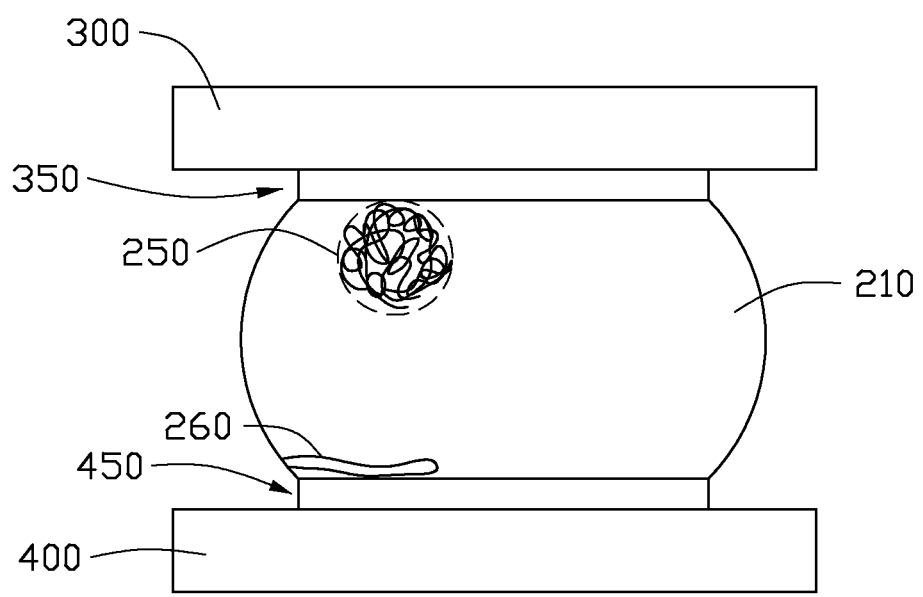
FIG. 3 is one embodiment of a partial cross section showing two boards connected by a solder ball by a non-destructive testing method.

FIG. 3 is a partial cross section showing an upper board 300 and a lower board 400 connected by a solder ball 210. The upper contacting portion 350 is positioned between the upper board 300 and the solder ball 210. The lower contacting portion 450 is positioned between the lower board 400 and the solder ball 210. For example, the upper board 300 and the lower board 400 can be the circuit device and the printed circuit board. The solder ball 210 includes at least one solder void 250 and at least one crack 260.

In one embodiment, the solder ball 210 is washed to remove residual flux originally used to used to degrease and decontaminate the surface thereof and prevent oxidization during soldering. A cleaning agent that can be used can be an isopropyl alcohol solution or a benzyl alcohol solution, in which solder ball 210 is immersed for a first predetermined time period. The washed solder ball 210 is immersed into a high absorbing material solution. A vacuum chamber vacuums and dries the washed solder ball 210. Finally, the X-ray machine reads the at least one solder void 250 and the at least one crack 260.

Figure 4:
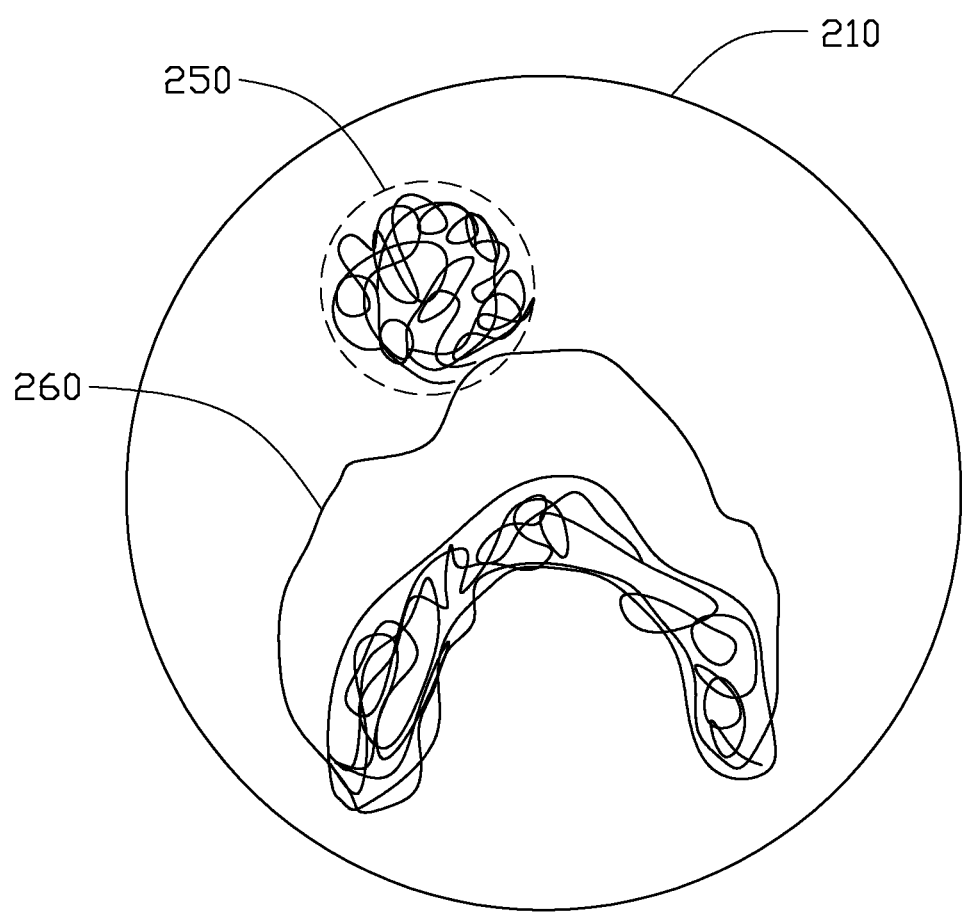
FIG. 4 is one embodiment of a horizontal scanography image detected by an X-ray machine.

As shown in FIG. 4, the horizontal scanography image of the solder ball 210 is detected by the X-ray machine. In the non-destructive testing method, the high absorption material penetrates at least one solder void 250 and the crack 260 after the solder ball 210 is subjected to vacuum. Irrespective of volume and thickness, the X-ray machine can detect the at least one solder void 250 and crack 260 in the horizontal scanography image of the solder ball 210.

Figure 5:
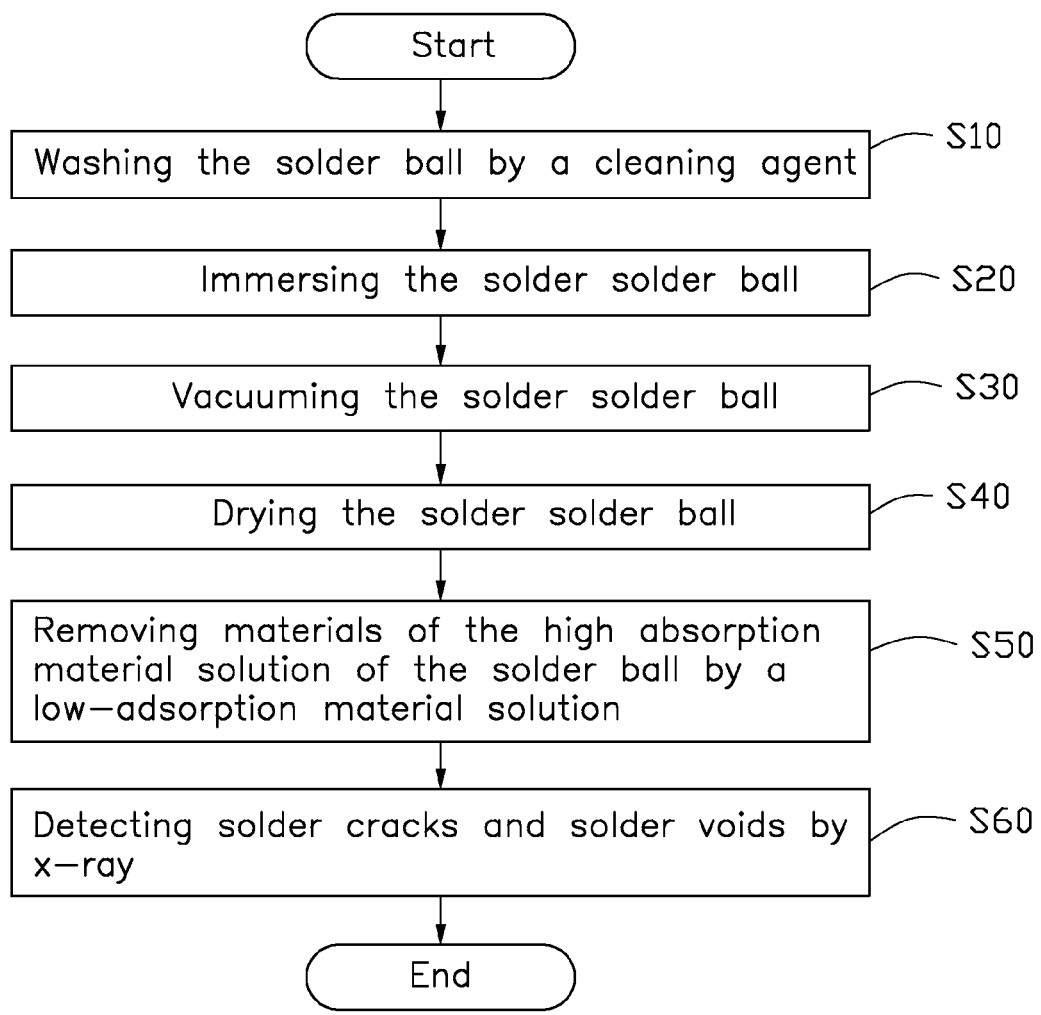
FIG. 5 is a flowchart of one embodiment of a non-destructive testing method.

FIG. 5 is a embodiment of a flowchart illustrating an embodiment of a method for detecting cracks in the solder ball 210. Depending on the embodiment, additional blocks may be added, others deleted, and the ordering of blocks may be changed.

In block S10, the solder ball 210 is washed and residual flux removed there from by a cleaning agent such as an isopropyl alcohol solution or a benzyl alcohol solution.

In block S20, the washed solder ball 210 is immersed into a high absorption material solution for a first predetermined time period, until the at least one solder void 250 and the least one crack 260 are immersed in the high absorption material solution entirely. In one embodiment, the first predetermined time period is set to 2-3 minutes. The high absorption material solution is a solution of a high absorption material highly absorbing X-rays, such as, for example, an acetone solution.

In block S30, the immersed solder ball is placed into a vacuum chamber. After vacuum is achieved, the high absorption material solution easily penetrates the at least one solder void 50 and the least one crack 260. As shown in FIG. 3, sections of the at least one solder void 50 and the at least one crack 260 of the solder ball 210 are fully penetrated after vacuum.

In block S40, the immersed solder ball is dried in the vacuum chamber at a fixed temperature for a second predetermined time period. The fixed temperature is preset to dry the immersed solder ball. The second predetermined time period is set as a time period until the immersed solder ball is fully dried corresponding to the set fixed temperature. In one embodiment, if the fixed temperature is set at 100° C., the second predetermined time period can be set as 3 hours according to an experience. In other embodiments, if the fixed temperature is set at 90° C., the second predetermined time period can be set as 4 hours according to needs.

In block S50, a material of the high absorption material solution near the surface of the solder ball 210 is removed by a low absorption material solution. In one embodiment, the low absorption material solution is a pure water solution.

In block S60, a X-ray machine detects the cracks 260 of the solder ball 210 by X-ray.

Material absorbing X-ray is characterized by the following formula:

$$I = I(0) * A(Z) * \mathrm{Exp}(-dx/C)$$

Where, I is an absorption intensity of the X-ray of a sample; I(0) is an X-ray radiation intensity of the X-ray machine;

A(Z) is the absorption coefficient of materials;
dx is a penetration depth of the X-ray in the sample; and
C is an attenuation coefficient of the X-ray.

From the equation, it can be seen that a radiation intensity passing though the solder ball 210 is I(0)−I. When materials with different absorption coefficients are radiated by the X-ray machine, material with a higher absorption coefficient adsorbs more X-ray. A section of the solder void 250 and the crack 260 with the high absorption material is detected as a darker color in a detected image by the X-ray machine. Otherwise, the section of the material with a lower absorption coefficient is detected as a light color in the detected image by the X-ray machine.

As shown in FIG. 4, the solder ball 210 is immersed into the high absorption material solution, dried in the vacuum chamber, and high absorption material is filled in the solder void 250 and the at least one crack 260. As shown in FIG. 4, the high absorption material is detected as a darker section in the detected image indicating the at least one solder void 250 and crack 260 with a small thickness.

Although certain inventive embodiments of the present disclosure have been specifically described, the present disclosure is not to be construed as being limited thereto. Various changes or modifications may be made to the present disclosure without departing from the scope and spirit of the present disclosure.

What is claimed is:

1. A method for detecting cracks and solder voids of a solder ball, comprising:
   immersing the solder ball into a high absorption material solution for a first predetermined time period, wherein the high absorption material solution is a solution of a high absorption material that absorbs X-rays;
   drying the immersed solder ball in a vacuum chamber at a fixed temperature for a second predetermined time period;
   removing materials of the high absorption material solution of the solder ball by a low absorption material solution, wherein the low absorption material solution is a solution of a low absorption material that absorbs less X-rays than the high absorption material, and an absorption coefficient of the low absorption material is less than an absorption coefficient of the high absorption material; and
   detecting the cracks and the solder voids by X-ray.

2. The method of claim 1, further comprising washing the solder ball by a cleaning agent.

3. The method of claim 2, wherein the cleaning agent is an isopropyl alcohol solution.

4. The method of claim 1, wherein the high absorption material solution is an acetone solution.

5. The method of claim 1, wherein the low absorption material solution is a pure water solution.

6. The method of claim 1, wherein the first predetermined time period is set as 2-3 minutes.

7. The method of claim 1, wherein the fixed temperature is set as 100° C.

8. The method of claim 7, wherein the second predetermined time period is set as three hours.

9. The method of claim 1, wherein the fixed temperature is set as 90° C.

10. The method of claim 9, wherein the second predetermined time period is set as four hours.

* * * * *